United States Patent
Ando et al.

(10) Patent No.: US 10,730,861 B2
(45) Date of Patent: Aug. 4, 2020

(54) PROCESS FOR PRODUCING EPOXY ALCOHOL COMPOUND

(71) Applicant: SUMITOMO CHEMICAL COMPANY, LIMITED, Chuo-ku (JP)

(72) Inventors: Kenichi Ando, Osaka (JP); Yohei Tanaka, Osaka (JP); Koh Kawami, Kurashiki (JP)

(73) Assignee: SUMITOMO CHEMICAL COMPANY, LIMITED, Chuo-ku (JP)

( * ) Notice: Subject to any disclaimer, the term of this patent is extended or adjusted under 35 U.S.C. 154(b) by 0 days.

(21) Appl. No.: 16/636,852

(22) PCT Filed: Jul. 25, 2018

(86) PCT No.: PCT/JP2018/027835
§ 371 (c)(1),
(2) Date: Feb. 5, 2020

(87) PCT Pub. No.: WO2019/031240
PCT Pub. Date: Feb. 14, 2019

(65) Prior Publication Data
US 2020/0172520 A1   Jun. 4, 2020

(30) Foreign Application Priority Data
Aug. 10, 2017 (JP) .................. 2017-155066

(51) Int. Cl.
*C07D 405/06* (2006.01)
*C07D 301/03* (2006.01)
*C07D 303/04* (2006.01)

(52) U.S. Cl.
CPC ......... *C07D 405/06* (2013.01); *C07D 301/03* (2013.01); *C07D 303/04* (2013.01)

(58) Field of Classification Search
CPC ... C07D 405/06; C07D 301/03; C07D 303/04
USPC ...................................................... 548/268.8
See application file for complete search history.

(56) References Cited

U.S. PATENT DOCUMENTS

| | | | |
|---|---|---|---|
| 5,637,727 A | 6/1997 | Jones et al. | |
| 6,133,485 A | 10/2000 | Singh et al. | |
| 2003/0236419 A1 | 12/2003 | Wang et al. | |
| 2004/0106810 A1 | 6/2004 | Bertolini et al. | |
| 2006/0155136 A1 | 7/2006 | Okuro et al. | |

FOREIGN PATENT DOCUMENTS

| | | |
|---|---|---|
| JP | 7-500569 A | 1/1995 |
| JP | 10-212287 A | 8/1998 |
| JP | 2004-513934 A | 5/2004 |
| WO | WO 2004/000826 A1 | 12/2003 |
| WO | WO 2012/053659 A1 | 4/2012 |

OTHER PUBLICATIONS

International Search Report dated Sep. 11, 2018 in PCT/JP2018/027835 filed Jul. 25, 2018.
International Preliminary Report on Patentability and Written Opinion dated Feb. 11, 2020, in PCT/JP2018/027835, 7 pages.

*Primary Examiner* — Kristin A Vajda
(74) *Attorney, Agent, or Firm* — Oblon, McClelland, Maier & Neustadt, L.L.P.

(57) ABSTRACT

A compound represented by formula (II):

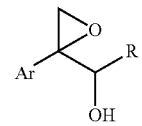

(II)

(where Ar represents a phenyl group optionally substituted by 1 to 3 substituents selected from the group consisting of a halogen atom and a trifluoromethyl group, and R represents a hydrogen atom or an alkyl group having 1 to 12 carbon atoms)
is produced by
step A: reacting trimethyl oxosulfonium salt or trimethyl sulfonium salt with a base in a solvent, and removing the resulting solid to obtain a trimethyl oxosulfonium ylide solution or a trimethyl sulfonium ylide solution; and
step B: reacting a compound represented by formula (I):

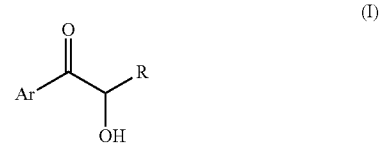

(I)

and the solution obtained in step A,
and the compound represented by formula (II) can be derived to a compound represented by formula (V):

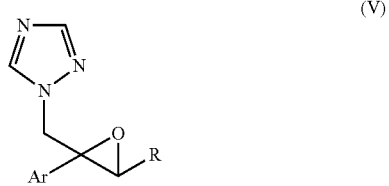

(V)

that is useful for production of an antifungal agent.

15 Claims, No Drawings

PROCESS FOR PRODUCING EPOXY ALCOHOL COMPOUND

TECHNICAL FIELD

The present invention relates to a process for producing an epoxy alcohol compound.

BACKGROUND ART

Epoxy alcohol compounds such as 3-(2,4-difluorophenyl)-3,4-epoxy-2-butanol and triazole compounds such as (2R,3S)-2-(2,4-difluorophenyl)-3-methyl-2-[(1H-1,2,4-triazol-1-yl)methyl]oxirane are known to be useful, for example, as production intermediates of antifungal agents (see, for example, WO2007/062542, U.S. Pat. Nos. 5,620,994, and 5,807,854).

With regard to a method for obtaining an epoxy alcohol compound and an epoxy triazole compound, U.S. Pat. No. 6,884,892 discloses a method of reacting 2',4'-difluoro-2-hydroxypropiophenone with trimethyl oxosulfonium salt in the presence of a base to obtain 3-(2,4-difluorophenyl)-3,4-epoxy-2-butanol which is an epoxy alcohol compound and further discloses a process for producing 2-(2,4-difluorophenyl)-3-methyl-2-[(1H-1,2,4-triazol-1-yl)methyl]oxirane which is an epoxy triazole compound via the epoxy alcohol compound.

SUMMARY OF THE INVENTION

However, in the above-described process for producing an epoxy alcohol compound, an isomer mixture with an undesired structural isomer may be obtained. As a process for producing a high-purity triazole compound from such an isomer mixture, WO2012/053659 discloses a method of decomposing a by-product structural isomer with an acid. However, in addition to an increase in the number of reaction steps, a desired yield of the epoxy alcohol compound decreases due to by-product formation of the originally undesired structural isomer. Therefore, in order to produce an epoxy triazole compound with a higher yield, it is required to reduce a by-production amount of the undesired structural isomer.

The present invention provides a process for producing an epoxy alcohol compound with a high yield and also provides a process for producing an epoxy triazole compound.

MODE FOR CARRYING OUT THE INVENTION

The present invention is as follows.
[1] A process for producing a compound (II), comprising: step A: reacting trimethyl oxosulfonium salt or trimethyl sulfonium salt with a base in a solvent, and removing the resulting solid to obtain a trimethyl oxosulfonium ylide solution or a trimethyl sulfonium ylide solution; and step B: reacting a compound (hereinafter referred to as compound (I)) represented by formula (I)

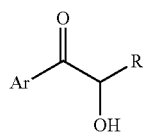

(I)

(where Ar represents a phenyl group optionally substituted by 1 to 3 substituents selected from the group consisting of a halogen atom and a trifluoromethyl group, and R represents a hydrogen atom or an alkyl group having 1 to 12 carbon atoms) and the trimethyl oxosulfonium ylide solution or trimethyl sulfonium ylide solution obtained in step A to obtain a compound (hereinafter referred to as compound (II)) represented by formula (II)

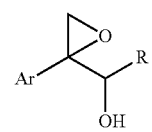

(II)

(where each symbol is as defined above).
[2] The process according to [1], in which the compound (I) is a compound represented by formula (Ia)

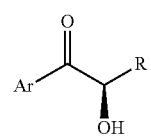

(Ia)

(where each symbol is as defined above), and the compound (II) is a compound represented by formula (IIa)

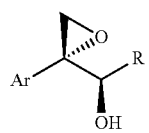

(IIa)

(where each symbol is as defined above).
[3] The process according to [1] or [2], in which Ar is a 2,4-difluorophenyl group or a 2,5-difluorophenyl group.
[4] The process according to [3], in which R is a methyl group.
[5] The process according to any one of [1] to [4], in which a solvent for reacting the trimethyl oxosulfonium salt or trimethyl sulfonium salt with the base in step A is tetrahydrofuran, dimethyl sulfoxide, toluene, or a mixed solvent thereof.
[6] A process for producing a compound (III) or its salt, comprising step A, step B and step C: reacting the compound (II) with 1,2,4-triazole in the presence of a base to obtain a compound (hereinafter referred to as compound (III)) represented by formula (III)

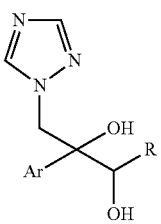

(III)

(where each symbol is as defined above) or its salt.

[7] The process according to [6], in which a compound (I) is a compound represented by formula (Ia), the compound (II) is a compound represented by formula (IIa), and the compound (III) is a compound represented by formula (IIIa)

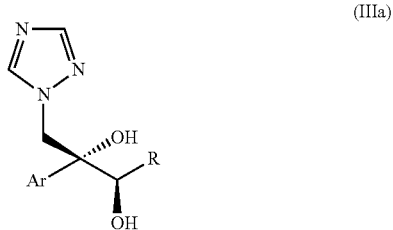

(IIIa)

(where each symbol is as defined above).

[8] The process according to [6] or [7], in which Ar is a 2,4-difluorophenyl group or a 2,5-difluorophenyl group.

[9] The process according to [8], in which R is a methyl group.

[10] The process according to any one of [6] to [9], in which a solvent for reacting the trimethyl oxosulfonium salt or trimethyl sulfonium salt with the base in step A is tetrahydrofuran, dimethyl sulfoxide, toluene, or a mixed solvent thereof.

[11] A process for producing a compound (IV) or its salt, comprising step A, step B, step C and step D: converting a primary or secondary hydroxyl group of the compound (III) or its salt into a leaving group to obtain a compound (hereinafter referred to as compound (IV)) represented by formula (IV)

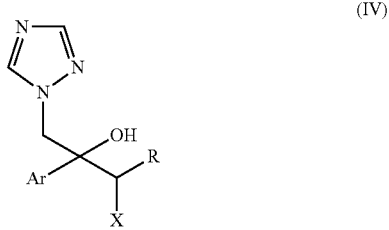

(IV)

(where X represents a leaving group, and Ar and R are as defined above) or its salt.

[12] The process according to [11], in which a compound (I) is a compound represented by formula (Ia), a compound (II) is a compound represented by formula (IIa), the compound (III) is a compound represented by formula (IIIc), and the compound (IV) is a compound represented by formula (IVa)

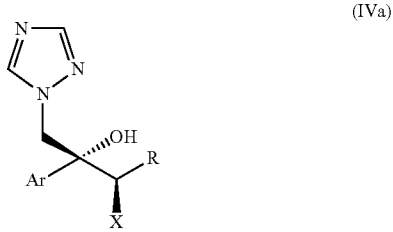

(IVa)

(where each symbol is as defined above).

[13] The process according to [11] or [12], in which Ar is a 2,4-difluorophenyl group or a 2,5-difluorophenyl group.

[14] The process according to [13], in which R is a methyl group.

[15] The process according to any one of [11] to [14], in which a solvent for reacting the trimethyl oxosulfonium salt or trimethyl sulfonium salt with the base in step A is tetrahydrofuran, dimethyl sulfoxide, toluene, or a mixed solvent thereof.

[16] A process for producing a compound (V) or its salt, comprising step A, step B, step C, step D and step E: reacting the compound (IV) or its salt with a base to obtain a compound (hereinafter referred to as compound (V)) represented by formula (V)

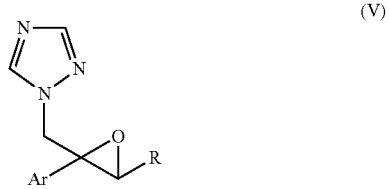

(V)

(where each symbol is as defined above) or its salt.

[17] The process according to [16], in which a compound (I) is a compound represented by formula (Ia), a compound (II) is a compound represented by formula (IIa), a compound (III) is a compound represented by formula (IIIc), the compound (IV) is a compound represented by formula (IVa), and the compound (V) is a compound represented by formula (Va)

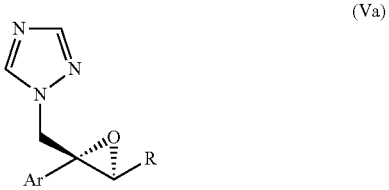

(Va)

(where each symbol is as defined above).

[18] The process according to [16] or [17], in which Ar is a 2,4-difluorophenyl group or a 2,5-difluorophenyl group.

[19] The process according to [18], in which R is a methyl group.

[20] The process according to any one of [16] to [19], in which a solvent for reacting the trimethyl oxosulfonium salt or trimethyl sulfonium salt with the base in step A is tetrahydrofuran, dimethyl sulfoxide, toluene, or a mixed solvent thereof.

[21] A process for producing a compound (VI), comprising step A, step B and step F: converting a hydroxyl group of a compound (II) into a leaving group to obtain a compound (hereinafter referred to as compound (VI)) represented by formula (VI)

(VI)

(where each symbol is as defined above).

[22] The process according to [21], in which a compound (I) is a compound represented by formula (Ia), the compound (II) is a compound represented by formula (IIa), and the compound (VI) is a compound represented by formula (VIa)

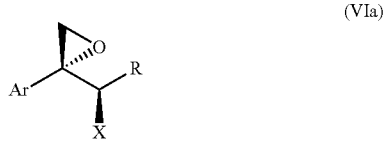

(where each symbol is as defined above).
[23] The process according to [21] or [22], in which Ar is a group selected from the group consisting of a 2,4-difluorophenyl group and a 2,5-difluorophenyl group.
[24] The process according to [21], in which R is a methyl group.
[25] The process according to any one of [21] to [24], in which a solvent for reacting the trimethyl oxosulfonium salt or trimethyl sulfonium salt with the base in step A is tetrahydrofuran, dimethyl sulfoxide, toluene, or a mixed solvent thereof.
[26] A process for producing a compound (V) or its salt, comprising step A, step B, step F and step G: reacting a compound (VI) with 1,2,4-triazole in the presence of a base to obtain the compound (V) or its salt.
[27] The process according to [26], in which a compound (I) is a compound represented by formula (Ia), a compound (II) is a compound represented by formula (IIa), a compound (VI) is a compound represented by formula (VIa), and the compound (V) is a compound represented by formula (Va).
[28] The process according to [26] or [27], in which Ar is a 2,4-difluorophenyl group or a 2,5-difluorophenyl group.
[29] The process according to [28], in which R is a methyl group.
[30] The process according to any one of [26] to [29], in which a solvent for reacting the trimethyl oxosulfonium salt or trimethyl sulfonium salt with the base in step A is tetrahydrofuran, dimethyl sulfoxide, toluene, or a mixed solvent thereof.

A halogen atom means a fluorine atom, a chlorine atom, a bromine atom or an iodine atom.

In a phenyl group optionally substituted by 1 to 3 substituents selected from the group consisting of a halogen atom and a trifluoromethyl group, a fluorine atom is preferred as the halogen atom. Examples of the phenyl group optionally substituted by 1 to 3 substituents selected from the group consisting of a halogen atom and a trifluoromethyl group include a phenyl group, a 2-fluorophenyl group, a 3-fluorophenyl group, a 4-fluorophenyl group, a 2-chlorophenyl group, a 3-chlorophenyl group, a 4-chlorophenyl group, a 4-bromophenyl group, a 4-iodophenyl group, a 2,3-difluorophenyl group, a 2,4-difluorophenyl group, a 2,5-difluorophenyl group, a 3,4-difluorophenyl group, a 3,5-difluorophenyl group, a 2,6-difluorophenyl group, a 2,3-dichlorophenyl group, a 2,4-dichlorophenyl group, a 3,4-dichlorophenyl group, a 3,5-dichlorophenyl group, a 2,6-dichlorophenyl group, a 2,4-dibromophenyl group, a 2,4,6-trifluorophenyl group, a 2-trifluoromethylphenyl group, a 3-trifluoromethylphenyl group a 4-trifluoromethylphenyl group, a 2,4-bis(trifluoromethyl)phenyl group, a 2,5-bis(trifluoromethyl)phenyl group, a 3,5-bis(trifluoromethyl)phenyl group, and a 2,4,6-tris(trifluoromethyl)phenyl group, and preferred examples include a 2,4-difluorophenyl group and a 2,5-difluorophenyl group.

The alkyl group having 1 to 12 carbon atoms means a linear or branched chain alkyl group having 1 to 12 carbon atoms. Examples thereof include a methyl group, an ethyl group, a propyl group, an isopropyl group, a butyl group, an isobutyl group, a sec-butyl group, a tert-butyl group, a pentyl group, an isopentyl group, a neopentyl group, a hexyl group, a heptyl group, an octyl group, a nonyl group, a decyl group, an undecyl group, and a dodecyl group. Among these groups, an alkyl group having 1 to 3 carbon atoms is preferred, and a methyl group is particularly preferred.

Examples of the trimethyl oxosulfonium salt include trimethyl oxosulfonium chloride, trimethyl oxosulfonium bromide, trimethyl oxosulfonium iodide, and trimethyl oxosulfonium methylsulfate. From the viewpoint of easy availability, trimethyl oxosulfonium bromide and trimethyl oxosulfonium iodide are preferred.

Examples of the trimethyl sulfonium salt include trimethyl sulfonium chloride, trimethyl sulfonium bromide, trimethyl sulfonium iodide, and trimethyl sulfonium methylsulfate. From the viewpoint of easy availability, trimethyl sulfonium bromide and trimethyl sulfonium iodide are preferred.

Examples of the leaving group include $-OS_2R^1$ ($R^1$ represents an optionally substituted alkyl group having 1 to 12 carbon atoms or an optionally substituted phenyl group), and preferred examples include $-OSO_2CH_3$. The alkyl group having 1 to 12 carbon atoms in an optionally substituted alkyl group having 1 to 12 carbon atoms in $R^1$ means a linear or branched chain alkyl group having 1 to 12 carbon atoms.

Examples of substituents in the optionally substituted alkyl group having 1 to 12 carbon atoms in $R^1$ include a halogen atom, and preferred examples include a fluorine atom. Examples of the optionally substituted alkyl group having 1 to 12 carbon atoms in $R^1$ include a methyl group, an ethyl group, a propyl group, an isopropyl group, a butyl group, an isobutyl group, a sec-butyl group, a tert-butyl group, a pentyl group, an isopentyl group, a neopentyl group, a hexyl group, a heptyl group, an octyl group, a nonyl group, a decyl group, an undecyl group, a dodecyl group, a fluoromethyl group and a trifluoromethyl group. Among these groups, a methyl group and a trifluoromethyl group are preferred.

Examples of substituents in an optionally substituted phenyl group in $R^1$ include an alkyl group having 1 to 12 carbon atoms and a halogen atom, and preferred examples include a methyl group. Examples of the optionally substituted phenyl group in $R^1$ include a phenyl group, a 2-methylphenyl group, a 3-methylphenyl group, a 4-methylphenyl group, a 4-ethylphenyl group, a 4-propylphenyl group, a 4-isopropylphenyl group, a 2-chlorophenyl group, a 3-chlorophenyl group, a 4-chlorophenyl group, a 4-fluorophenyl group and a 4-bromophenyl group, and the preferred example is a 4-methylphenyl group.

In the compounds (I), (II), (III), (IV), (V) and (VI) in the present invention, Ar is a 2,4-difluorophenyl group or 2,5-difluorophenyl group, and R is particularly preferably a methyl group.

The compounds (I), (II), (III), (IV), (V) and (VI) in the present invention may have one or more asymmetric carbon atoms. The compounds (I), (II), (III), (IV), (V) and (VI) in the present invention include any optically active form and mixtures thereof (such as racemate, enantiomeric mixture, and diastereomeric mixture).

In the compounds (I), (II), (III), (IV), (V) and (VI), the respective compounds having preferred configurations are compounds represented respectively by formulas (Ia), (IIa), (IIIa), (IVa), (Va) and (VIa).

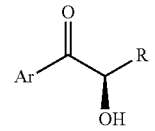
(Ia)

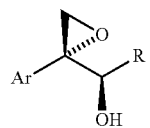
(IIa)

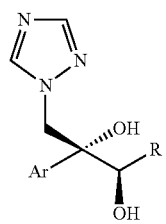
(IIIa)

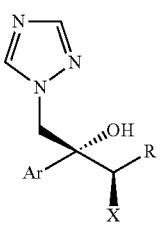
(IVa)

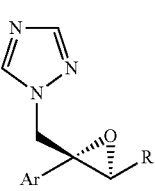
(Va)

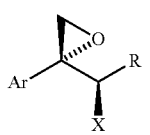
(VIa)

(where each symbol is as defined above.)

The compounds (III), (IV) and (V) have a 1,2,4-triazole ring and may be in the form of a salt. Examples of the salts of the compounds (III), (IV) and (V) include addition salts of hydrochloric acid, hydrobromic acid, sulfuric acid, methanesulfonic acid, paratoluenesulfonic acid, oxalic acid, succinic acid, fumaric acid, maleic acid, phthalic acid, and phosphoric acid.

A summary of the production process of the present invention is shown in the following scheme.

Trimethyl oxosulfonium salt
or
trimethyl sulfonium salt

↓ Base, Remove Solid | Step A

Solution containing trimethyl oxosulfonium ylide or trimethyl sulfonium ylide

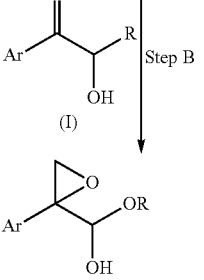
(I)

↓ Step B

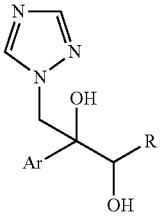
(II)

Step F ↙ ↘ Step C (triazole NH, Base)

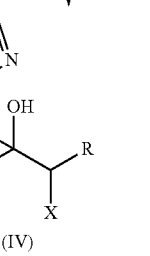
(III)

↓ Step D (VI) → Step G (triazole NH, Base) → (V) ← Step E ← (IV)

(where each symbol is as defined above.)

1. Process for Producing Trimethyl Oxosulfonium Ylide Solution or Trimethyl Sulfonium Ylide Solution (Step A)

In step A, trimethyl oxosulfonium salt or trimethyl sulfonium salt and a base are reacted in a solvent, and the resulting solid is removed to obtain a trimethyl oxosulfonium ylide solution or a trimethyl sulfonium ylide solution.

The reaction is generally carried out by mixing trimethyl oxosulfonium salt or trimethyl sulfonium salt and a base in a solvent. In the mixing of trimethyl oxosulfonium salt or trimethyl sulfonium salt and a base, the mixing order is not particularly limited, and, for example, a method of adding the base to a mixture of a solvent and trimethyl oxosulfonium salt or trimethyl sulfonium salt; and a method of adding trimethyl oxosulfonium salt or trimethyl sulfonium salt to a mixture of the solvent and the base can be adopted.

Examples of the base used in step A include alkali metal hydroxides such as potassium hydroxide, sodium hydroxide and lithium hydroxide; alkali metal hydrides such as sodium hydride, potassium hydride and lithium hydride; alkyl alkali metals such as butyl lithium, methyl lithium, and hexyl lithium; alkali metal amides such as sodium amide, potassium amide, lithium diisopropylamide, lithium dicyclohexylamide, and lithium hexamethyldisilazide; and alkali metal alkoxides such as potassium tert-butoxide, sodium tert-butoxide, sodium methoxide, sodium ethoxide, potassium methoxide, and potassium ethoxide, and the preferred example is sodium hydride.

Sodium hydride may be dispersed in mineral oil such as liquid paraffin and the like and added dropwise.

The amount of the base used in step A is usually a proportion of 0.25 mol to 1.1 mol, preferably 0.5 mol to 1.0 mol, relative to 1 mol of trimethyl oxosulfonium salt or trimethyl sulfonium salt.

Examples of the solvent used in step A include ether solvents such as tetrahydrofuran (THF), methyl tert-butyl ether (MTBE), 1,4-dioxane, diethylene glycol dimethyl ether (diglyme), ethylene glycol dimethyl ether, 1,3-dioxolane, and 2-methyltetrahydrofuran; aprotonic polar solvents such as N,N-dimethylformamide (DMF), N,N-dimethylacetamide (DMAc), dimethyl sulfoxide (DMSO), N-methyl-2-pyrrolidinone (NMP), 1,3-dimethyl-2-imidazolydinone (DMI), acetonitrile and propionitrile; halogenated hydrocarbon solvents such as monochlorobenzene, 1,2-dichlorobenzene and monofluorobenzene; aromatic hydrocarbon solvents such as toluene and xylene, mineral oils such as liquid paraffin and mixed solvents thereof, and the preferred examples include tetrahydrofuran (THF), toluene, dimethyl sulfoxide (DMSO), a mixed solvent of tetrahydrofuran (THF) and toluene, a mixed solvent of tetrahydrofuran (THF) and dimethyl sulfoxide (DMSO) and a mixed solvent of toluene and dimethyl sulfoxide (DMSO).

The amount of the solvent used is usually a proportion of 0.5 L to 50 L, preferably 1 L to 30 L, and more preferably 2 L to 25 L, relative to 1 kg of a trimethyl oxosulfonium salt or trimethyl sulfonium salt.

The reaction in step A is carried out at usually $-10°$ C. to $100°$ C., preferably $-5°$ C. to $80°$ C., more preferably $0°$ C. to $60°$ C., for usually 0.5 hours to 24 hours, preferably 1 hour to 8 hours.

The reaction of trimethyl oxosulfonium salt or trimethyl sulfonium salt with a base in a solvent and removal of the resulting solid are performed by, for example, a method of reacting trimethyl oxosulfonium salt or trimethyl sulfonium salt with the base in the solvent and then removing the resulting solid by filtration or collecting a supernatant portion.

In order to improve the yield of trimethyl oxosulfonium ylide or trimethyl sulfonium ylide, after removal, the removed solid may be washed with a solvent, and the obtained washing liquid and the previously obtained filtrate may be combined. When washing is performed, the solvent used in the washing is preferably the solvent used in the reaction of step A. The amount of the solvent used for washing is usually a proportion of 0.5 L to 10 L, relative to 1 kg of a trimethyl oxosulfonium salt or trimethyl sulfonium salt.

In step B, by using a solution containing trimethyl oxosulfonium ylide or trimethyl sulfonium ylide, which is obtained by reacting trimethyl oxosulfonium salt or trimethyl sulfonium salt with a base in a solvent and removing the resulting solid, in the reaction of step B, it is possible to suppress by-product formation of a compound (hereinafter referred to as compound (VII)) represented by the formula (VII)

(where each symbol is as defined above.) which is a structural isomer of the compound (II).

2. Process for Producing Compound (II) (Step B)

In step B, the compound (II) is obtained by reacting the compound (I) with the trimethyl oxosulfonium ylide solution or trimethyl sulfonium ylide solution obtained in step A.

The reaction is generally carried out by mixing the compound (I) with the trimethyl oxosulfonium ylide solution or trimethyl sulfonium ylide solution obtained in step A. Specific examples include a method of adding the trimethyl oxosulfonium ylide solution or trimethyl sulfonium ylide solution obtained in step A to the compound (I); and a method of adding the compound (I) to the obtained trimethyl oxosulfonium ylide solution or trimethyl sulfonium ylide solution. The method of adding the compound (I) to the obtained trimethyl oxosulfonium ylide solution or trimethyl sulfonium ylide solution is preferred.

The compound (I) is usually used as a solution mixed with a solvent. Examples of the solvent include ether solvents such as tetrahydrofuran (THF), methyl tert-butyl ether (MTBE), 1,4-dioxane, diethylene glycol dimethyl ether (diglyme), ethylene glycol dimethyl ether, 1,3-dioxolane, and 2-methyltetrahydrofuran; aprotonic polar solvents such as N,N-dimethylformamide (DMF), N,N-dimethylacetamide (DMAc), dimethyl sulfoxide (DMSO), sulfolane, N-methyl-2-pyrrolidinone (NMP), 1,3-dimethyl-2-imidazolydinone (DMI), hexamethylphosphoric triamide (HMPA), nitrobenzene, carbon disulfide, acetonitrile and propionitrile; halogenated hydrocarbon solvents such as methylene chloride, 1,2-dichloroethane, monochlorobenzene, 1,2-dichlorobenzene, 2-chlorotoluene, 3-chlorotoluene, 4-chlorotoluene, 2-chloro-m-xylene, 2-chloro-p-xylene, 4-chloro-o-xylene, 2,3-dichlorotoluene, 2,4-dichlorotoluene, 2,5-dichlorotoluene, 2,6-dichlorotoluene, 3,4-dichlorotoluene, and monofluorobenzene; aromatic hydrocarbon solvents such as toluene and xylene; and mixed solvents thereof, and the preferred example is toluene.

The trimethyl oxosulfonium ylide solution or trimethyl sulfonium ylide solution obtained in step A may be used as a solution further mixed with a solvent. Examples of the solvent are the same as those described for the compound (I).

The amount of the solvent used in step B is usually a proportion of 0.5 L to 50 L, preferably 1 L to 30 L, more preferably 2 L to 25 L, relative to 1 kg of the compound (I).

The amount of the trimethyl oxosulfonium ylide solution or trimethyl sulfonium ylide solution used in step B is usually a proportion of 0.8 mol to 5.0 mol, preferably 1.0 mol to 3.0 mol, more preferably 1.0 mol to 2.0 mol, relative to 1 mol of the compound (I), based on the amount of trimethyl oxosulfonium ylide or trimethyl sulfonium ylide contained in the solution.

The concentration of trimethyl oxosulfonium ylide or trimethyl sulfonium ylide in a solution containing trimethyl oxosulfonium ylide or trimethyl sulfonium ylide can be easily determined by a conventional method. For example, the method described in Encyclopedia of Reagents for Organic Synthesis Second Edition, p 4336 can be referred to.

The reaction in step B is carried out at usually −40° C. to 120° C., preferably −20° C. to 60° C., more preferably −10° C. to 40° C., for usually 0.5 hours to 24 hours, preferably 1 hour to 8 hours.

The compound (II) obtained in step B can be isolated and purified by a conventional method. For example, the compound (II) can be isolated by mixing a reaction mixture with water, followed by liquid separation, washing an organic layer with an acidic aqueous solution and/or basic aqueous solution, and drying and concentrating under reduced pressure.

After the isolation, the compound (II) may be purified by, for example, silica gel column chromatography. The compound (II) may be subjected to step C or step F without purification.

The compound (I) can be produced by the method described in U.S. Pat. No. 6,884,892 and the like.

In step B, the optically active form of the compound (II) can be obtained by using the optically active form of the compound (I). For example, a compound represented by the formula (IIa) can be obtained by using the compound represented by the formula (Ia) in step B.

3. Process for Producing Compound (III) or its Salt (Step C)

In step C, the compound (III) is obtained by reacting the compound (II) with 1,2,4-triazole in the presence of a base.

The reaction is usually carried out by mixing the compound (II) and 1,2,4-triazole in a solvent in the presence of a base. In the mixing of the compound (II) and 1,2,4-triazole in the presence of a base, the mixing order of the reagents is not particularly limited. For example, a method of adding a solvent, the base, and 1,2,4-triazole to the compound (II); a method of mixing the solvent, 1,2,4-triazole, and the base and then adding the compound (II); and a method of adding a solution, reacted by adding the base to a mixture of the solvent and 1,2,4-triazole, to a mixture of the solvent and the compound (II) can be adopted.

The base used in step C is not particularly limited, and examples thereof include alkali metal hydroxides such as sodium hydroxide, potassium hydroxide, and lithium hydroxide; alkali metal carbonates such as potassium carbonate, sodium carbonate, lithium carbonate and cesium carbonate; alkali metal hydrides such as sodium hydride, potassium hydride and lithium hydride; alkyl alkali metals such as butyl lithium, methyl lithium, and hexyl lithium; alkali metal amides such as sodium amide, potassium amide, lithium diisopropylamide, lithium dicyclohexylamide, and lithium hexamethyldisilazide; alkali metal alkoxides such as potassium tert-butoxide, sodium tert-butoxide, potassium methoxide, sodium methoxide, sodium ethoxide, and potassium ethoxide; and tertiary amines such as 1,8-diazabicyclo[5.4.0]-7-undecene, 1,5-diazabicyclo[4.3.0]-5-nonene, 1,4-diazabicyclo[2.2.2]-octane, N,N,N'N'-tetramethylethylenediamine, N,N-diisopropylethylamine, and trimethylamine. The preferred examples include sodium hydride and potassium carbonate. Sodium hydride may be dispersed in mineral oil such as liquid paraffin and the like and added dropwise.

The amount of 1,2,4-triazole used in step C is usually a proportion of 0.8 mol to 5.0 mol, preferably 1.0 mol to 3.0 mol, more preferably 1.1 mol to 2.0 mol, relative to 1 mol of the compound (II).

The amount of the base used in step C is usually a proportion of 0.05 to 1.3 mol, preferably 0.1 to 1.1 mol, more preferably 0.15 to 1.0 mol, relative to 1 mol of 1,2,4-triazole.

In order to facilitate the reaction, for example, a phase transfer catalyst may be added, and examples thereof include tetraalkylammonium salts such as octadecyltrimethylammonium bromide, tetrabutylammonium sulfate, tetrabutylammonium bromide, tetrabutylammonium iodide and tetrabutylammonium chloride; and trialkylbenzylammonium salts such as benzyltrimethylammonium bromide, benzyltrimethylammonium chloride, and benzyltriethylammonium chloride.

The solvent used in step C may be one that is inert to the reaction, and examples thereof include ether solvents such as THF, methyl tert-butyl ether, 1,4-dioxane, diethylene glycol dimethyl ether (diglyme), ethylene glycol dimethyl ether, 1,3-dioxolane, and 2-methyltetrahydrofuran; aprotic polar solvents such as DMF, DMAc, DMSO, sulfolane, NMP, DMI, HMPA, methyl isobutyl ketone, methyl ethyl ketone, acetone, cyclohexanone, 3-pentanone, nitrobenzene, carbon disulfide, acetonitrile and propionitrile; halogenated hydrocarbon solvents such as methylene chloride, 1,2-dichloroethane, monochlorobenzene, 1,2-dichlorobenzene, 2-chlorotoluene, 3-chlorotoluene, 4-chlorotoluene, 2-chloro-m-xylene, 2-chloro-p-xylene, 4-chloro-o-xylene, 2,3-dichlorotoluene, 2,4-dichlorotoluene, 2,5-dichlorotoluene, 2,6-dichlorotoluene, 3,4-dichlorotoluene, and monofluorobenzene; aromatic hydrocarbon solvents such as toluene and xylene; and mixed solvents thereof. The preferred example is methyl ethyl ketone.

The amount of the solvent used is usually a proportion of 1 L to 50 L, preferably 1.5 L to 30 L, more preferably 2 L to 20 L, relative to 1 kg of the compound (II).

The reaction in step C is carried out at usually −20° C. to 150° C., preferably 0° C. to 100° C., more preferably 20° C. to 90° C., for usually 0.5 hours to 24 hours, preferably 1 hour to 10 hours.

The compound (III) obtained in step C can be isolated and purified by a conventional method. For example, the compound (III) can be isolated by mixing a reaction mixture with water, followed by liquid separation, washing and drying the organic layer, and concentrating under reduced pressure. After the isolation, the compound (II) may be purified by, for example, silica gel column chromatography.

A salt of the compound (III) may be obtained by adding an acid to the obtained compound (III). Examples of the acid added include hydrochloric acid, hydrobromic acid, sulfuric acid, methanesulfonic acid, paratoluenesulfonic acid, oxalic acid, succinic acid, fumaric acid, maleic acid, phthalic acid, and phosphoric acid. The amount of the acid used is usually a proportion of 1 mol to 5 mol, relative to 1 mol of the compound (III).

The compound (III) or its salt may be subjected to step D without purification.

As the compound (II) used in step C, for example, the compound obtained in step B can be used. In step C, the optically active form of the compound (III) or a salt of the optically active form of the compound (III) can be obtained by using the optically active form of the compound (II). For example, a compound represented by the formula (IIIc) can be obtained by using the compound represented by the formula (IIa) in step C.

4. Process for Producing Compound (IV) or its Salt (Step D)

In step D, a primary or secondary hydroxyl group of the compound (III) or its salt is converted into a leaving group to obtain the compound (IV). Examples of the leaving group include a sulfonyloxy group (—OSO$_2$R$^1$), and the preferred example is —OSO$_2$CH$_3$.

Step D can be specifically performed by converting the primary or secondary hydroxyl group of the compound (III) or its salt into a sulfonyloxy group (—OSO$_2$R$^1$). Here, R$^1$ is as defined above.

In step D, the method of converting the primary or secondary hydroxyl group of the compound (III) or its salt into a sulfonyloxy group includes, for example, a method of reacting the compound (III) or its salt with sulfonic acid halide (hereinafter referred to as sulfonic acid halide (XI)) represented by the formula (XI):

YSO$_2$R$^1$ (XI)

(where Y represents a chlorine atom or a bromine atom, and R$^1$ is as defined above), or a sulfonic acid anhydride (hereinafter referred to as sulfonic acid anhydride (XII)) represented by the formula (XII):

O(SO$_2$R$^1$)$_2$ (XII)

(where R$^1$ is as defined above)
in a solvent in the presence of a base. The reaction is usually carried out by mixing the compound (III) or its salt with sulfonic acid halide (XI) or sulfonic anhydride (XII) in a solvent in the presence of a base. In the mixing of the compound (III) or its salt with sulfonic acid halide (XI) or sulfonic anhydride (XII) in the presence of a base, the mixing order of the reagents is not particularly limited. The compound (III) or its salt can be mixed with sulfonic acid halide (XI) or sulfonic anhydride (XII) in the presence of a base by, for example, a method of mixing the compound (III) or its salt with the base in a solvent and then adding sulfonic acid halide (XI) or sulfonic anhydride (XII); or a method of mixing the solvent, the compound (III) or its salt with sulfonic acid halide (XI) or sulfonic anhydride (XII) and then adding the base. However, the method of mixing the compound (III) or its salt with the base in the solvent and then adding sulfonic acid halide (XI) or sulfonic anhydride (XII) is desirable in that a side reaction in which a tertiary hydroxyl group is converted into a sulfonyloxy group can be suppressed.

The amount of sulfonic acid halide (XI) or sulfonic anhydride (XII) used in step D is usually a proportion of 0.8 mol to 5.0 mol, preferably 1.0 mol to 3.0 mol, more preferably 1.0 mol to 2.0 mol, relative to 1 mol of the compound (III) or its salt.

Examples of the base used in step D include aliphatic tertiary amines such as trimethylamine, triethylamine, tributylamine, diisopropylethylamine, and N-methylmorpholine; aromatic amines such as pyridine, picoline, 2,6-lutidine, collidine, 4-(N,N-dimethylamino)pyridine, N,N-dimethylaniline, and N,N-diethylaniline; alkali metal carbonates such as sodium carbonate and potassium carbonate; and basic ion exchange resins such as Amberlite IRA-67 and Amberlite IRA-900. Triethylamine or sodium carbonate is preferred, and triethylamine is particularly preferred.

When the compound (III) is used, the amount of the base used in step D is usually a proportion of 0.8 mol to 3.0 mol, preferably 1.0 mol to 2.0 mol, more preferably 1.0 mol to 1.5 mol, relative to 1 mol of sulfonic acid halide (XI) or sulfonic acid anhydride (XII). When the salt of the compound (III) is used, the amount of the base is usually a proportion of 1.8 mol to 8.0 mol, preferably 2.0 mol to 5.0 mol, more preferably 2.0 mol to 2.5 mol, relative to 1 mol of sulfonic acid halide (XI) or sulfonic acid anhydride (XII).

The solvent used in step D may be one that is inert to the reaction, and examples thereof include methylene chloride, 1,2-dichloroethane, monochlorobenzene, 1,2-dichlorobenzene, 2-chlorotoluene, 3-chlorotoluene 4-chlorotoluene, 2-chloro-m-xylene, 2-chloro-p-xylene, 4-chloro-o-xylene, 2,3-dichlorotoluene, 2,4-dichlorotoluene, 2,5-dichlorotoluene 2,6-dichlorotoluene, 3,4-dichlorotoluene, monofluorobenzene, nitrobenzene, carbon disulfide, toluene, acetonitrile, propionitrile, methyl tert-butyl ether, ethylene glycol dimethyl ether, diethylene glycol dimethyl ether, tetrahydrofuran, 2-methyl tetrahydrofuran, 1,3-dioxolane, 1,4-dioxane and mixed solvents thereof, and the preferred example is toluene.

The amount of the solvent used is usually a proportion of 0.5 L to 50 L, preferably 1 L to 30 L, more preferably 2 L to 25 L, relative to 1 kg of the compound (III) or its salt.

The reaction in step D is carried out at usually −30° C. to 80° C., preferably −10° C. to 60° C., more preferably −5° C. to 30° C., for usually 0.5 hours to 24 hours, preferably 1 hour to 10 hours.

The compound (IV) obtained in step D can be isolated and purified by a conventional method. For example, the compound (IV) can be isolated by pouring a reaction mixture into water, followed by liquid separation, washing and drying the organic layer, and concentrating under reduced pressure. After the isolation, the compound (II) may be purified by, for example, silica gel column chromatography.

A salt of the compound (IV) may be obtained by adding an acid to the compound (IV) obtained in step D. Examples of the acid added include hydrochloric acid, hydrobromic acid, sulfuric acid, methanesulfonic acid, paratoluenesulfonic acid, oxalic acid, succinic acid, fumaric acid, maleic acid, phthalic acid, and phosphoric acid. The amount of the acid used is usually a proportion of 1 mol to 5 mol, relative to 1 mol of the compound (IV).

The compound (IV) or its salt may be subjected to step E without purification.

As the compound (III) or its salt used in step D, for example, the compound obtained in step C can be used. In step D, the optically active form of the compound (IV) or its salt can be obtained by using the optically active form of the compound (III) or its salt. For example, a compound represented by the formula (IVa) can be obtained by using the compound represented by the formula (IIIa) in step D.

5. Process for Producing Compound (V) or its Salt (Step E)

In step E, the compound (V) is obtained by reacting the compound (IV) or its salt with a base.

The reaction can usually be carried out by mixing the compound (IV) or its salt and a base in a solvent. In the mixing of the compound (IV) or its salt with a base, the order of addition of the reagents is not particularly limited. The compound (IV) or its salt can be mixed with a base by, for example, a method of adding the compound (IV) or its salt to a mixture of a solvent and the base; or a method of adding the base to a mixture of the solvent and the compound (IV) or its salt. The mixture of the solvent and the base may be added to the mixture of the solvent and the compound (IV) or its salt.

Examples of the base used in step E include alkali metal hydroxides such as sodium hydroxide, potassium hydroxide, and lithium hydroxide; alkali metal carbonates such as potassium carbonate, sodium carbonate, lithium carbonate and cesium carbonate; alkali metal hydrides such as sodium hydride, potassium hydride and lithium hydride; alkyl alkali metals such as butyl lithium, methyl lithium, and hexyl lithium; alkali metal amides such as sodium amide, potassium amide, lithium diisopropylamide, lithium dicyclohexylamide, and lithium hexamethyldisilazide; alkali metal alkoxides such as potassium tert-butoxide, sodium tert-butoxide, sodium methoxide, sodium ethoxide, potassium methoxide, and potassium ethoxide; and aliphatic tertiary amines such as trimethylamine, triethylamine, tributylamine, diisopropylethylamine, and N-methylmorpholine, and the preferred examples include sodium hydroxide and triethylamine. Sodium hydroxide may be used by dissolving in water.

When the compound (IV) is used, the amount of the base used in step E is usually a proportion of 0.8 mol to 15 mol, preferably 1.5 mol to 10 mol, more preferably 2 mol to 5 mol, relative to 1 mol of the compound (IV). When the salt of the compound (IV) is used, the amount of the base is usually a proportion of 1.8 mol to 20 mol, preferably 2.5 mol to 13 mol, more preferably 3 mol to 6 mol, relative to 1 mol of the salt of the compound (IV).

In order to facilitate the reaction, a phase transfer catalyst may be added, and examples thereof include tetraalkylammonium salts such as octadecyltrimethylammonium bromide, tetrabutylammonium sulfate, tetrabutylammonium bromide, tetrabutylammonium iodide and tetrabutylammonium chloride; and trialkylbenzylammonium salts such as benzyltrimethylammonium bromide, benzyltrimethylammonium chloride, and benzyltriethylammonium chloride.

The solvent used in step E may be one that is inert to the reaction, and examples thereof include ether solvents such as THF, methyl tert-butyl ether, 1,4-dioxane, diethylene glycol dimethyl ether (diglyme), ethylene glycol dimethyl ether, 1,3-dioxolane, and 2-methyltetrahydrofuran; aprotonic polar solvents such as DMF, DMAc, DMSO, sulfolane, NMP, DMI, HMPA, methyl isobutyl ketone, methyl ethyl ketone, acetone, cyclohexanone, 3-pentanone, nitrobenzene, carbon disulfide, acetonitrile and propionitrile; halogenated hydrocarbon solvents such as methylene chloride, 1,2-dichloroethane, monochlorobenzene, 1,2-dichlorobenzene, 2-chlorotoluene, 3-chlorotoluene, 4-chlorotoluene, 2-chloro-m-xylene, 2-chloro-p-xylene, 4-chloro-o-xylene, 2,3-dichlorotoluene, 2,4-dichlorotoluene, 2,5-dichlorotoluene, 2,6-dichlorotoluene, 3,4-dichlorotoluene, and monofluorobenzene; aromatic hydrocarbon solvents such as toluene and xylene; and mixed solvents thereof, and the preferred example is tetrahydrofuran (THF).

The amount of the solvent used is usually a proportion of 0.5 L to 50 L, preferably 0.75 L to 30 L, more preferably 1 L to 25 L, relative to 1 kg of the compound (IV) or its salt.

The reaction in step E is carried out at usually −20° C. to 150° C., preferably 0° C. to 100° C., more preferably 10° C. to 70° C., for usually 0.5 hours to 24 hours, preferably 1 hour to 10 hours.

The compound (V) obtained in step E can be isolated and purified by a conventional method. For example, the compound (V) can be isolated by mixing a reaction mixture with water, followed by liquid separation, washing and drying the organic layer, and concentrating under reduced pressure. After the isolation, the compound (V) may be purified by, for example, silica gel column chromatography or recrystallization.

A salt of the compound (V) may be obtained by adding an acid to the compound (V) obtained in step E. Examples of the acid added include hydrochloric acid, hydrobromic acid, sulfuric acid, methanesulfonic acid, paratoluenesulfonic acid, oxalic acid, succinic acid, fumaric acid, maleic acid, phthalic acid, and phosphoric acid. The amount of the acid used is usually a proportion of 1 mol to 5 mol, relative to 1 mol of the compound (V).

The compound (V) or its salt may be subjected to a reaction that leads to a target antifungal agent without purification.

As the compound (IV) or its salt used in step E, for example, the compound obtained in step D can be used. In step E, the optically active form of the compound (V) or its salt can be obtained by using the optically active form of the compound (IV) or its salt. For example, a compound represented by the formula (Va) can be obtained by using the compound represented by the formula (IVa) in step E.

6. Process for Producing Compound (VI) (Step F)

In step F, a hydroxyl group of the compound (II) is converted into a leaving group to obtain the compound (VI). Examples of the leaving group include a sulfonyloxy group ($-OS_2R^1$), and the preferred example is $-OSO_2CH_3$.

Step F can be specifically performed by converting the hydroxyl group of the compound (II) into a sulfonyloxy group ($-OSO_2R^1$). Here, $R^1$ is as defined above.

In step F, the method of converting the hydroxyl group of the compound (II) into a sulfonyloxy group includes, for example, a method of reacting the compound (II) with sulfonic acid halide (XI) or sulfonic acid anhydride (XII) in a solvent in the presence of a base. The reaction is usually carried out by mixing the compound (II) with sulfonic acid halide (XI) or sulfonic anhydride (XII) in a solvent in the presence of a base. In the mixing of the compound (II) with sulfonic acid halide (XI) or sulfonic anhydride (XII) in the presence of a base, the mixing order of the reagents is not particularly limited. The compound (II) and sulfonic acid halide (XI) or sulfonic acid anhydride (XII) can be mixed in the presence of a base by, for example, a method of mixing the compound (II) and the base in a solvent and then adding sulfonic acid halide (XI) or sulfonic anhydride (XII); or a method of mixing the solvent, the compound (II), and sulfonic acid halide (XI) or sulfonic anhydride (XII) and then adding the base.

The amount of sulfonic acid halide and the like used in step F is usually a proportion of 0.8 mol to 3.0 mol, preferably 1.0 mol to 2.0 mol, more preferably 1.0 mol to 1.5 mol, relative to 1 mol of the compound (II).

Examples of the base used in step F include aliphatic tertiary amines, aromatic amines, alkali metal carbonates, and basic ion exchange resins. Triethylamine or sodium carbonate is preferred, and triethylamine is particularly preferred.

The amount of the base used in step F is usually a proportion of 0.8 mol to 3.0 mol, preferably 1.0 mol to 2.0 mol, more preferably 1.0 mol to 1.5 mol, relative to 1 mol of sulfonic acid halide (XI) or sulfonic anhydride (XII).

The solvent used in step F may be one that is inert to the reaction, and examples thereof include methylene chloride, 1,2-dichloroethane, monochlorobenzene, 1,2-dichlorobenzene, 2-chlorotoluene, 3-chlorotoluene 4-chlorotoluene, 2-chloro-m-xylene, 2-chloro-p-xylene, 4-chloro-o-xylene, 2,3-dichlorotoluene, 2,4-dichlorotoluene, 2,5-dichlorotoluene 2,6-dichlorotoluene, 3,4-dichlorotoluene, monofluorobenzene, nitrobenzene, carbon disulfide, toluene, acetonitrile, propionitrile, methyl tert-butyl ether, ethylene glycol dimethyl ether, diethylene glycol dimethyl ether, tetrahydrofuran, 2-methyl tetrahydrofuran, 1,3-dioxolane, 1,4-dioxane and mixed solvents thereof, and the preferred example is toluene.

The amount of the solvent used is usually a proportion of 1 L to 50 L, preferably 4 L to 30 L, more preferably 5 L to 25 L, relative to 1 kg of the compound (II).

The reaction in step F is carried out at usually −30° C. to 80° C., preferably −10° C. to 60° C., more preferably −5° C. to 30° C., for usually 0.5 hours to 24 hours, preferably 1 hour to 10 hours.

The compound (VI) obtained in step F can be isolated and purified by a conventional method. For example, the compound (VI) can be isolated by mixing a reaction mixture with water, followed by liquid separation, washing and drying the organic layer, and concentrating under reduced pressure. After the isolation, the compound (II) may be purified by, for example, silica gel column chromatography. The compound (VI) may be subjected to step G without purification.

As the compound (II) used in step F, for example, the compound obtained in step B can be used. In step F, the optically active form of the compound (VI) can be obtained by using the optically active form of the compound (II). For example, a compound represented by the formula (VIa) can be obtained by using the compound represented by the formula (IIa) in step F.

7. Process for Producing Compound (V) or its Salt (Step G)

In step G, the compound (V) is obtained by reacting the compound (VI) with 1,2,4-triazole in the presence of a base.

The reaction is usually carried out by mixing the compound (VI) and 1,2,4-triazole in a solvent in the presence of a base. In the mixing of the compound (VI) and 1,2,4-triazole in the presence of a base, the order of addition of the reagents is not particularly limited. The compound (VI) and 1,2,4-triazole can be mixed in the presence of a base by, for example, a method of mixing a solvent, 1,2,4-triazole, and the base and then adding the compound (VI); or a method of adding a solution, reacted by adding the base to a mixture of the solvent and 1,2,4-triazole, to a mixture of the solvent and the compound (VI).

The amount of 1,2,4-triazole used in step G is usually a proportion of 0.8 mol to 5.0 mol, preferably 1.0 mol to 3.0 mol, more preferably 1.1 mol to 2.0 mol, relative to 1 mol of the compound (VI).

The base used in step G is not particularly limited, and examples thereof include alkali metal hydroxide, alkali metal carbonate, alkali metal hydride, alkyl alkali metal, alkali metal amide and alkali metal alkoxide. Preferred examples include sodium hydride, potassium carbonate and sodium methoxide. Sodium hydride may be dispersed in mineral oil such as liquid paraffin and the like and added dropwise.

The amount of the base used in step G is usually a proportion of 0.3 mol to 1.3 mol, preferably 0.5 mol to 1.1 mol, more preferably 0.8 mol to 1.0 mol, relative to 1 mol of 1,2,4-triazole.

In order to facilitate the reaction, a phase transfer catalyst may be added, and examples thereof include tetraalkylammonium salts such as octadecyltrimethylammonium bromide, tetrabutylammonium sulfate, tetrabutylammonium bromide, tetrabutylammonium iodide and tetrabutylammonium chloride; and trialkylbenzylammonium salts such as benzyltrimethylammonium bromide, benzyltrimethylammonium chloride, and benzyltriethylammonium chloride.

The solvent used in step G may be one that is inert to the reaction, and examples thereof include ether solvents such as THF, methyl tert-butyl ether, 1,4-dioxane, diethylene glycol dimethyl ether (diglyme), ethylene glycol dimethyl ether, 1,3-dioxolane, and 2-methyltetrahydrofuran; aprotic polar solvents such as DMF, DMAc, DMSO, sulfolane, NMP, DMI, HMPA, methyl isobutyl ketone, methyl ethyl ketone, acetone, cyclohexanone, 3-pentanone, nitrobenzene, carbon disulfide, acetonitrile and propionitrile; halogenated hydrocarbon solvents such as methylene chloride, 1,2-dichloroethane, monochlorobenzene, 1,2-dichlorobenzene, 2-chlorotoluene, 3-chlorotoluene, 4-chlorotoluene, 2-chloro-m-xylene, 2-chloro-p-xylene, 4-chloro-o-xylene, 2,3-dichlorotoluene, 2,4-dichlorotoluene, 2,5-dichlorotoluene, 2,6-dichlorotoluene, 3,4-dichlorotoluene, and monofluorobenzene; aromatic hydrocarbon solvents such as toluene and xylene; and mixed solvents thereof, and the preferred example is DMF.

The amount of the solvent used is usually a proportion of 0.5 L to 50 L, preferably 0.75 L to 30 L, more preferably 1 L to 25 L, relative to 1 kg of the compound (VI).

The reaction in step G is carried out at usually −20° C. to 150° C., preferably 0° C. to 100° C., more preferably 20° C. to 90° C., for usually 0.5 hours to 24 hours, preferably 1 hour to 10 hours.

The compound (V) obtained in step G can be isolated and purified by a conventional method. For example, the compound (V) can be isolated by mixing a reaction mixture with water, followed by liquid separation, washing and drying the organic layer, and concentrating under reduced pressure. After the isolation, the compound (V) may be purified by, for example, silica gel column chromatography or recrystallization.

A salt of the compound (V) may be obtained by adding an acid to the compound (V) obtained in step G. Examples of the acid added include hydrochloric acid, hydrobromic acid, sulfuric acid, methanesulfonic acid, paratoluenesulfonic acid, oxalic acid, succinic acid, fumaric acid, maleic acid, phthalic acid, and phosphoric acid. The amount of the acid used is usually a proportion of 1 mol to 5 mol, relative to 1 mol of the compound (V).

The compound (V) or its salt may be subjected to a reaction that leads to a target antifungal agent without purification.

As the compound (VI) used in step G, for example, the compound obtained in step F can be used. In step G, the optically active form of the compound (V) or its salt can be obtained by using the optically active form of the compound (VI). For example, a compound represented by the formula (Va) can be obtained by using the compound represented by the formula (VIa) in step G.

The compound (V) can be derived into a triazole compound useful as an antifungal agent according to a known method. In that case, for example, JP-A-4-356471, U.S. Pat. No. 5,177,094 and the like can be referred to.

EXAMPLES

The present invention will be illustrated by the following examples, which do not limit the present invention.

In the following examples, the obtained compound (II) was analyzed according to the following conditions, and its content was determined by an absolute calibration curve method.

<Analysis Conditions of High-Performance Liquid Chromatography (HPLC)>

Column: YMC-Pack ODS-A, 4.6 mmφ×100 mm, S-3 μm, 12 nm

Mobile Phase:

liquid A: distilled water or ion exchanged water liquid B: acetonitrile/2-propanol=95/5 (v/v)

Gradient Condition:

TABLE 1

| | Time (min) | | | |
|---|---|---|---|---|
| | 0 | 15 | 50 | 50.01 |
| Concentration of liquid B in mobile phase (%) | 18 | 18 | 70 | 18 |

Flow rate: 1.5 mL/min
Column temperature: 35° C.
Detection wavelength: 254 nm
Sample-diluting solution: acetonitrile/2-propanol=1/1 (v/v)
Injection amount: 15 μL
Retention time:

TABLE 2

| Compound | Retention time (min) |
|---|---|
| (R)-1-(2,4-difluorophenyl)-2-hydroxy-1-propanone | About 9 min |
| (2R,3R)-3-(2,4-difluorophenyl)-3,4-epoxy-2-butanol | About 12 min |
| 1-(2,4-difluorophenyl)-1-(2-methyl-2-oxiranyl)methanol | About 15 min |
| (R)-1-(2,5-difluorophenyl)-2-hydroxy-1-propanone | About 8 min |
| (2R,3R)-3-(2,5-difluorophenyl)-3,4-epoxy-2-butanol | About 12 min |
| 1-(2,5-difluorophenyl)-1-(2-methyl-2-oxiranyl)methanol | About 14 min |

Example 1

Step A 124.46 g of trimethyl oxosulfonium bromide, 304.44 g of THF and 54.79 g of liquid paraffin were mixed, and the temperature was raised to about 50° C. Thereafter, 24.76 g of sodium hydride (about 60° mineral oil dispersion) was added by portions, followed by stirring while maintaining the temperature until foaming of hydrogen stopped. A solid matter was separated from the resulting slurry by filtration, and the residue was washed with 194.84 g of THF to obtain 568.26 g of a THF solution of trimethyl oxosulfonium ylide.

Step B 527.65 g of the THF solution of trimethyl oxosulfonium ylide obtained in step A and 259.94 g of toluene were mixed and cooled to 0° C. A mixture of 128.29 g (0.537 mol, content: 78.0%) of (R)-1-(2,4-difluorophenyl)-2-hydroxy-1-propanone and 69.52 g of toluene was added dropwise to the resulting mixture over 5 hours. In addition, the portion adhered to an instrument was washed with 17.40 g of toluene. As a result of HPLC analysis, the weight of (2R,3R)-3-(2,4-difluorophenyl)-3,4-epoxy-2-butanol in the resulting reaction mixture was 94.52 g (0.472 mol, yield: 87.9%). A ratio of 1-(2,4-difluorophenyl)-1-(2-methyl-2-oxiranyl)methanol and (2R,3R)-3-(2,4-difluorophenyl)-3,4-epoxy-2-butanol as structural isomers was 5.05:94.95. A mixture prepared by dissolving 22.58 g of citric acid monohydrate in 200.00 g of water and 43.30 g of toluene were separately added dropwise to the resulting mixture at 0° C. The temperature was raised to 25° C., and the resulting mixture was stirred, followed by liquid separation. Next, the organic layer was washed with a weak alkaline aqueous solution, prepared by dissolving 2.26 g of sodium bicarbonate in 100.00 g of water, and 100.00 g of water, and 942.69 g of a THF-toluene solution of (2R,3R)-3-(2,4-difluorophenyl)-3,4-epoxy-2-butanol was obtained. As a result of HPLC analysis, the weight of (2R,3R)-3-(2,4-difluorophenyl)-3,4-epoxy-2-butanol in this solution was 91.75 g (0.458 mol, yield: 85.3%). The ratio of 1-(2,4-difluorophenyl)-1-(2-methyl-2-oxiranyl)methanol and (2R,3R)-3-(2,4-difluorophenyl)-3,4-epoxy-2-butanol as the structural isomers was 5.33:94.67.

Example 2

Step A 124.46 g of trimethyl oxosulfonium bromide, 304.44 g of THF and 54.79 g of liquid paraffin were mixed, and the temperature was raised to about 50° C. Thereafter, 24.76 g of sodium hydride (about 60% mineral oil dispersion) was added by portions, followed by stirring while maintaining the temperature until foaming of hydrogen stopped. A solid matter was separated from the resulting slurry by filtration, and the residue was washed with 194.84 g of THF to obtain 559.86 g of a THF solution of trimethyl oxosulfonium ylide.

Step B 89.69 g of the THF solution of trimethyl oxosulfonium ylide obtained in step A and 48.71 g of toluene were mixed and cooled to 0° C. A mixture of 21.87 g (0.0940 mol, content: 80.0%) of (R)-1-(2,5-difluorophenyl)-2-hydroxy-1-propanone and 12.12 g of toluene was added dropwise to the resulting mixture over 5 hours. In addition, the portion adhered to an instrument was washed with 3.03 g of toluene. As a result of HPLC analysis, the weight of (2R,3R)-3-(2,5-difluorophenyl)-3,4-epoxy-2-butanol in the resulting reaction mixture was 15.59 g (0.0779 mol, yield: 82.8°). A ratio of 1-(2,5-difluorophenyl)-1-(2-methyl-2-oxiranyl)methanol and (2R,3R)-3-(2,5-difluorophenyl)-3,4-epoxy-2-butanol as structural isomers was 1.92:98.08. A mixture prepared by dissolving 8.30 g of citric acid monohydrate in 153.13 g of water and 7.58 g of toluene were separately added dropwise to the resulting mixture at 0° C. The temperature was raised to 25° C., and the resulting mixture was stirred, followed by liquid separation. The resulting aqueous layer was further extracted with 62.14 g of toluene, and the resulting organic layers were combined. Next, the organic layer was washed with a weak alkaline aqueous solution prepared by dissolving 0.39 g of sodium bicarbonate in 71.75 g of water and further washed twice with 71.75 g of water, and 228.75 g of a THF-toluene solution of (2R,3R)-3-(2,5-difluorophenyl)-3,4-epoxy-2-butanol was obtained. As a result of HPLC analysis, the weight of (2R,3R)-3-(2,5-difluorophenyl)-3,4-epoxy-2-butanol in this solution was 15.26 g (0.0762 mol, yield: 81.1%). The ratio of 1-(2,5-difluorophenyl)-1-(2-methyl-2-oxiranyl)methanol and (2R,3R)-3-(2,5-difluorophenyl)-3,4-epoxy-2-butanol as the structural isomers was 1.32:98.68.

Example 3

Step A 27.19 g of trimethyl oxosulfonium iodide, 30.00 g of toluene, 30.00 g of DMSO and 9.20 g of liquid paraffin were mixed, and the temperature was lowered to 5° C. Thereafter, 4.27 g of sodium hydride (about 60° mineral oil dispersion) was added little by little, followed by stirring while maintaining the temperature until foaming of hydrogen stopped. 30.00 g of toluene was added dropwise to the resulting slurry, and the temperature was maintained. Thereafter, a solid matter was separated by filtration, and the residue was washed with 20.00 g of toluene to obtain 84.25 g of a toluene-DMSO solution of trimethyl oxosulfonium ylide.

Step B 37.16 g of a toluene-DMSO solution of trimethyl oxosulfonium ylide obtained in step A and 5.00 g of DMSO were mixed and cooled to 0° C. A mixture of 6.01 g (0.0269 mol, content: 82.3%) of (R)-1-(2,4-difluorophenyl)-2-hydroxy-1-propanone, 2.00 g of toluene and 4.50 g of DMSO was added dropwise to the resulting mixture over about 16 hours. In addition, the portion adhered to an instrument was washed with a mixed solution of 0.50 g of toluene and 0.50 g of DMSO. As a result of HPLC analysis, the weight of (2R,3R)-3-(2,4-difluorophenyl)-3,4-epoxy-2-butanol in the resulting reaction mixture was 4.04 g (0.0202 mol, yield: 75.2%). The ratio of 1-(2,4-difluorophenyl)-1-(2-methyl-2-oxiranyl)methanol and (2R,3R)-3-(2,4-difluorophenyl)-3,4-epoxy-2-butanol as the structural isomers was 4.39:95.61. A mixture prepared by dissolving 1.13 g of citric acid monohydrate in 22.50 g of water was added dropwise to the resulting mixture. The temperature was raised to 25° C., and the resulting mixture was stirred, followed by liquid separation. The resulting aqueous layer was further extracted with 10.00 g of toluene and subsequently extracted with 5.00 g of toluene, and the resulting organic layers were combined. Next, the organic layer was washed with a weak alkaline aqueous solution, prepared by dissolving 0.11 g of sodium bicarbonate in 15.00 g of water, and 15.00 g of water, and 52.74 g of a toluene solution of (2R,3R)-3-(2,4-difluorophenyl)-3,4-epoxy-2-butanol was obtained. As a result of HPLC analysis, the weight of (2R,3R)-3-(2,4-difluorophenyl)-3,4-epoxy-2-butanol in this solution was 3.78 g (0.0189 mol, yield: 70.3%). The ratio of 1-(2,4-difluorophenyl)-1-(2-methyl-2-oxiranyl)methanol and (2R,3R)-3-(2,4-difluorophenyl)-3,4-epoxy-2-butanol as the structural isomers was 4.34:95.66.

Example 4

Step A 2.43 g of trimethyl oxosulfonium chloride, 8.00 g of THF and 0.65 g of sodium hydride (about 60% mineral oil dispersion) were mixed, and the temperature was raised to about 50° C., followed by stirring while maintaining the temperature until foaming of hydrogen stopped. A solid matter was separated from the resulting slurry by filtration, and the residue was washed with 5.12 g of THF to obtain 12.35 g of a THF solution of trimethyl oxosulfonium ylide.

Step B 4.23 g of the THF solution of trimethyl oxosulfonium ylide obtained in step A and 2.60 g of toluene were mixed and cooled to 0° C. A mixture of 1.20 g (0.00537 mol, content: 83.2%) of (R)-1-(2,4-difluorophenyl)-2-hydroxy-1-propanone and 0.69 g of toluene was added dropwise to the resulting mixture over 5 hours. In addition, the portion adhered to an instrument was washed with 0.17 g of toluene. As a result of HPLC analysis, the weight of (2R,3R)-3-(2,4-difluorophenyl)-3,4-epoxy-2-butanol in the resulting reaction mixture was 0.959 g (0.00479 mol, yield: 89.2°). The ratio of 1-(2,4-difluorophenyl)-1-(2-methyl-2-oxiranyl)methanol and (2R,3R)-3-(2,4-difluorophenyl)-3,4-epoxy-2-butanol as the structural isomers was 2.95:97.05. A mixture, prepared by dissolving 0.23 g of citric acid monohydrate in 4.00 g of water, and 4.00 g of toluene were separately added dropwise to the resulting mixture at 0° C. The temperature was raised to 25° C., and the resulting mixture was stirred, followed by liquid separation. Next, the organic layer was washed with a weak alkaline aqueous solution prepared by dissolving 0.02 g of sodium bicarbonate in 2.00 g of water and further washed with 2.00 g of water, and 10.91 g of a THF-toluene solution of (2R,3R)-3-(2,4-difluorophenyl)-3,4-epoxy-2-butanol was obtained. As a result of HPLC analysis, the weight of (2R,3R)-3-(2,4-difluorophenyl)-3,4-epoxy-2-butanol in this solution was 0.888 g (0.00444 mol, yield: 82.6%). The ratio of 1-(2,4-difluorophenyl)-1-(2-methyl-2-oxiranyl)methanol and (2R,3R)-3-(2,4-difluorophenyl)-3,4-epoxy-2-butanol as the structural isomers was 3.00:97.00.

Reference Example 1

For reference, when an operation of removing solids is not included, an experiment was performed by the following method.

9.50 g of trimethyl oxosulfonium iodide and 2.76 g of liquid paraffin were added to a mixture of 40.59 g of DMSO and 13.82 g of THF, and the temperature was lowered to 8° C. Thereafter, 1.37 g of sodium hydride (about 60% mineral oil dispersion) was added by portions. After hydrogen evolution ceased, the mixture was cooled to 3° C., and a mixture of 6.00 g (0.0322 mol, content: 83.1%) of (R)-1-(2,4-difluorophenyl)-2-hydroxy-1-propanone and 17.09 g of DMSO was slowly added dropwise at 3° C. As a result of HPLC analysis, the ratio of 1-(2,4-difluorophenyl)-1-(2-methyl-2-oxiranyl)methanol and (2R,3R)-3-(2,4-difluorophenyl)-3,4-epoxy-2-butanol as the structural isomers was 11.75:88.25.

Example 5

513.72 g (0.250 mol, content: 9.7%) of a THF-toluene solution of (2R,3R)-3-(2,4-difluorophenyl)-3,4-epoxy-2-butanol was concentrated under reduced pressure to obtain 124.19 g of an oily substance. 150.00 g of methyl ethyl ketone, 10.36 g of potassium carbonate and 25.88 g of 1,2,4-triazole were added to the obtained oily substance, and the mixture was kept warm at 65° C. for 8 hours. After cooling to room temperature, 50.00 g of water was added and stirred, followed by being allowed to stand. The organic layer was collected, 75.00 g of 20% normal brine and 75.00 g of toluene were added, and the mixture was stirred, followed by liquid separation. The resulting organic layer was concentrated under reduced pressure to obtain an oily substance containing (2R,3R)-2-(2,4-difluorophenyl)-1-(1H-1,2,4-triazol-1-yl)-2,3-butanediol.

Example 6

A mixture of 156.42 g of an oily substance containing (2R,3R)-2-(2,4-difluorophenyl)-1-(1H-1,2,4-triazol-1-yl)-2,3-butanediol, 134.20 g of THF, and 134.50 g of toluene was cooled to 0° C. After addition of 35.38 g of triethylamine, 40.05 g of methanesulfonyl chloride was slowly added dropwise at −5 to 5° C., and the mixture was kept warm for 1 hour. The temperature was raised to room temperature, and 201.76 g of 10% normal brine was added and stirred, followed by liquid separation. The organic layer was separated, and an aqueous solution obtained by dissolving 29.97 g of sodium hydroxide in 201.76 g of water was added dropwise. The mixture was stirred, followed by liquid separation. A mixture of 3.25 g of 35% hydrochloric acid and 23.54 g of water was added dropwise to the resulting organic layer, and the mixture was stirred, followed by liquid separation. The resulting organic layer was washed with a weak alkaline aqueous solution obtained by dissolving 1.47 g of sodium bicarbonate in 23.54 g of water, and concentrated under reduced pressure. The obtained oily substance, 50.38 g of 2-propanol and 36.32 g of heptane were mixed, and the temperature was raised to around 50° C., followed by cooling to precipitate crystals. Thereafter, the resulting mixture was cooled to 0° C. and kept warm. The resulting crystals were filtered, and the obtained crystals were washed with a mixed solution of 11.65 g of 2-propanol and 36.80 g of heptane and 46.00 g of heptane and dried to obtain 39.29 g of (2R,3S)-2-(2,4-difluorophenyl)-3-methyl-2-[(1H-1,2,4-triazol-1-yl)methyl]oxirane.

Example 7

228.75 g (0.0762 mol, content: 6.7%) of a THF-toluene solution of (2R,3R)-3-(2,5-difluorophenyl)-3,4-epoxy-2-butanol was concentrated under reduced pressure to obtain 33.64 g of an oily substance. 45.78 g of methyl ethyl ketone, 3.16 g of potassium carbonate and 7.90 g of 1,2,4-triazole were added to the obtained oily substance, and the mixture was kept warm at 65° C. for 8 hours. After cooling to room temperature, 22.89 g of water was added and stirred, followed by being allowed to stand. The organic layer was collected, 22.89 g of 20° normal brine and 22.89 g of toluene were added, and the mixture was stirred, followed by liquid separation to obtain 88.74 g of an organic layer. After 43.63 g of the resulting organic layer was concentrated under reduced pressure, 22.50 g of toluene and 11.25 g of THF were added, and the precipitated solid was filtered. The remaining solids were washed with a mixture of 7.50 g of toluene and 3.75 g of THF. A filtrate and a washing liquid were combined and then concentrated under reduced pressure to obtain an oily substance containing (2R,3R)-2-(2,5-difluorophenyl)-1-(1H-1,2,4-triazol-1-yl)-2,3-butanediol.

Example 8

A mixture of 16.17 g of an oily substance containing (2R,3R)-2-(2,5-difluorophenyl)-1-(1H-1,2,4-triazol-1-yl)-2,3-butanediol, 20.18 g of THF, and 20.18 g of toluene was cooled to 0° C. After addition of 4.17 g of triethylamine, 4.29 g of methanesulfonyl chloride was slowly added dropwise at 0 to 3° C. After maintaining the temperature for 2 hours, 0.42 g of triethylamine and 0.43 g of methanesulfonyl chloride were further added, and the temperature was maintained for 1 hour. The temperature was raised to room temperature, and 20.18 g of 10% normal brine was added and stirred, followed by liquid separation. The organic layer was separated, and an aqueous solution obtained by dissolving 3.00 g of sodium hydroxide in 20.18 g of water was added dropwise. The mixture was stirred, followed by liquid separation. 20.18 g of 20% normal brine was added to the resulting organic layer, and the mixture was stirred, followed by liquid separation. The resulting organic layer was washed twice with an acidic aqueous solution obtained by diluting 0.24 g of 35% hydrochloric acid with 3.53 g of water. The resulting organic layer was washed with a weak alkaline aqueous solution obtained by dissolving 0.33 g of sodium bicarbonate in 7.06 g of water, and concentrated under reduced pressure. The obtained oily substance and 30.26 g of toluene were mixed and washed with an acidic aqueous solution obtained by diluting 0.24 g of 35° hydrochloric acid with 3.53 g of water. The resulting organic layer was washed with an acidic aqueous solution obtained by diluting 0.12 g of 35° hydrochloric acid with 3.53 g of water. The resulting organic layer was washed with a weak alkaline aqueous solution obtained by dissolving 0.22 g of sodium bicarbonate in 7.06 g of water, and concentrated under reduced pressure. The obtained oily substance, 10.09 g of toluene and 10.09 g of MTBE were mixed, and the temperature was raised to around 40° C., followed by cooling to precipitate crystals. Thereafter, 10.09 g of heptane was added dropwise, and the resulting mixture was cooled to around 0° C. and kept warm for 2 hours, followed by filtering crystals. The obtained crystals were washed with a mixed solution of 5.05 g of MTBE and 10.09 g of heptane and 15.14 g of heptane and dried to obtain 5.94 g of (2R,3S)-2-(2,5-difluorophenyl)-3-methyl-2-[(1H-1,2,4-triazol-1-yl)methyl]oxirane.

Example 9

69.85 g (0.0600 mol, content: 17.2%) of a toluene solution of (2R,3R)-3-(2,4-difluorophenyl)-3,4-epoxy-2-butanol and 6.68 g of triethylamine were mixed, and the resulting mixture was cooled to 0° C. While maintaining the resulting mixture at a temperature of 0 to 10° C., 7.22 g of methanesulfonyl chloride was added dropwise. In addition, 0.61 g of triethylamine and 0.69 g of methanesulfonyl chloride were each added twice (after 16 hours and after a further 2.5 hours). After maintaining the temperature for 1 hour, 33.60 g of water was added, and the mixture was stirred, followed by liquid separation. The resulting organic layer was washed with 33.60 g of water and then washed with 33.60 g of 10% brine. The resulting mixture was concentrated under reduced pressure, and 11.34 g of DMF was added to the obtained oily substance to obtain a DMF solution of (R)-1-[(R)-2-(2,4-difluorophenyl)-2-oxiranyl]ethyl methanesulfonate.

Example 10

4.91 g of 1,2,4-triazole, 14.18 g of DMF and 4.80 g of liquid paraffin were mixed, and the temperature was cooled to 0 to 5° C. Thereafter, 2.59 g of sodium hydride (about 60% mineral oil dispersion) was added little by little while maintaining the temperature at 0 to 5° C., followed by stirring while maintaining the temperature until foaming of hydrogen stopped. The resulting mixture was warmed to around 40° C., and then cooled to room temperature to prepare a 1,2,4-triazole sodium salt slurry. Next, the prepared 1,2,4-triazole sodium salt slurry was added dropwise to 31.24 g of a DMF solution of (R)-1-[(R)-2-(2,4-difluorophenyl)-2-oxiranyl]ethyl methanesulfonate described in Example 9, which was kept warm at 45 to 50° C., and the portion adhered to an instrument was washed with 2.13 g of DMF. After the temperature of the resulting mixture was maintained at 40 to 45° C. for 14 hours, the mixture was cooled to room temperature. After the resulting reaction mixture was added dropwise to a mixed solution of 1.05 g of sodium chloride, 15.00 g of water and 23.38 g of toluene, the portion adhered to an instrument was washed with 6.00 g of water and 5.20 g of toluene. The resulting mixture was separated, and the aqueous layer was extracted sequentially with 18.19 g and 9.09 g of toluene. The resulting organic layers were combined and washed with strong alkaline water in which 0.086 g of sodium hydroxide was dissolved in 10.50 g of water. Next, washing was carried out twice with an acidic aqueous solution obtained by diluting 0.35 g of 35% hydrochloric acid with 5.25 g of water. Furthermore, washing was carried out with a weak alkaline aqueous solution obtained by dissolving 0.32 g of sodium bicarbonate in 10.50 g of water, and the resulting organic layer was concentrated under reduced pressure. 22.47 g of toluene and 7.90 g of heptane were added to the obtained oily substance and warmed to around 50° C., followed by cooling to precipitate crystals. Thereafter, the resulting mixture was cooled to around 5° C. and kept warm, followed by filtering crystals. The obtained crystals were washed with a mixed solution of 2.60 g of toluene and 8.21 g of heptane and 10.26 g of heptane and dried to obtain 7.01 g of (2R,3S)-2-(2,4-difluorophenyl)-3-methyl-2-[(1H-1,2,4-triazol-1-yl)methyl]oxirane.

Example 11

68.42 g (0.0500 mol, content: 14.6%) of a toluene solution of (2R,3R)-3-(2,5-difluorophenyl)-3,4-epoxy-2-butanol and 6.18 g of triethylamine were mixed, and the resulting mixture was cooled to 0° C. While maintaining the resulting mixture at a temperature of 0 to 10° C., 6.36 g of methanesulfonyl chloride was added dropwise, and the temperature was maintained for 2 hours. 31.11 g of water was added to the reaction mixture, and the mixture was stirred, followed by liquid separation. The resulting organic layer was washed with 33.60 g of water and then washed with 28.00 g of water. After 1.20 g of magnesium sulfate was added to the resulting organic layer and stirred, the mixture was filtered, and the remaining solids were washed with toluene. 14.55 g of DMF was added to the obtained filtrate and washing liquid, and the resulting mixture was concentrated under reduced pressure to obtain a DMF solution of (R)-1-[(R)-2-(2,5-difluorophenyl)-2-oxiranyl]ethyl methanesulfonate.

Example 12

6.42 g of 1,2,4-triazole, 13.14 g of DMF and 6.20 g of liquid paraffin were mixed, and the temperature was cooled to 0 to 5° C. Thereafter, 3.38 g of sodium hydride (about 60° mineral oil dispersion) was added little by little while maintaining the temperature at 0 to 5° C., followed by stirring while maintaining the temperature until foaming of hydrogen stopped. The resulting mixture was warmed to room temperature to prepare a 1,2,4-triazole sodium salt slurry. Next, the prepared 1,2,4-triazole sodium salt slurry was added dropwise to 38.07 g of a DMF solution of (R)-1-[(R)-2-(2,5-difluorophenyl)-2-oxiranyl]ethyl methanesulfonate described in Example 11, which was kept warm at around 50° C., and the portion adhered to an instrument was washed with 5.91 g of DMF. The resulting mixture was kept warm at around 50° C. for 4 hours. The resulting reaction mixture was cooled to room temperature, and after the resulting reaction mixture was added dropwise to a mixed solution of 0.97 g of normal salt, 13.90 g of water and 21.67 g of toluene, the portion adhered to an instrument was washed with 5.56 g of water and 4.82 g of toluene. The resulting mixture was separated, and the aqueous layer was extracted sequentially with 16.85 g and 8.43 g of toluene. The resulting organic layers were combined and washed twice with an acidic aqueous solution obtained by diluting 0.32 g of 35° hydrochloric acid with 4.87 g of water. Next, washing was carried out with a weak alkaline aqueous solution obtained by dissolving 0.29 g of sodium bicarbonate in 9.73 g of water, and the resulting organic layer was concentrated under reduced pressure. 22.39 g of toluene was added to the obtained oily substance and warmed to around 55° C., followed by adding 9.89 g of heptane. The resulting mixture was cooled to around 28° C. to precipitate crystals. Thereafter, the resulting mixture was cooled to around 10° C. and kept warm, followed by filtering crystals. The obtained crystals were washed with a mixed solution of 8.55 g of toluene and 12.27 g of heptane and 19.02 g of heptane and dried to obtain 5.75 g of (2R,3S)-2-(2,5-difluorophenyl)-3-methyl-2-[(1H-1,2,4-triazol-1-yl)methyl]oxirane.

INDUSTRIAL APPLICABILITY

According to the present invention, an epoxy alcohol compound and an epoxy triazole compound useful for production of an antifungal agent can be produced with a high yield while suppressing by-product formation of undesired structural isomers.

The invention claimed is:

1. A process for producing a compound represented by formula (II)

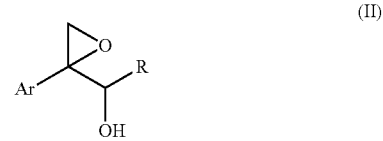

wherein Ar represents a phenyl group optionally substituted by 1 to 3 substituents selected from the group consisting of a halogen atom and a trifluoromethyl group, and R represents a hydrogen atom or an alkyl group having 1 to 12 carbon atoms, the process comprising:

a step A of reacting trimethyl oxosulfonium salt or trimethyl sulfonium salt with a base in a solvent, and removing the resulting solid to obtain a trimethyl oxosulfonium ylide solution or a trimethyl sulfonium ylide solution; and a step B of reacting a compound represented by formula (I)

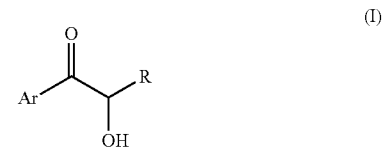

wherein Ar and R are as defined above, with the trimethyl oxosulfonium ylide solution or trimethyl sulfonium ylide solution obtained in the step A to obtain the compound represented by formula (II).

2. The process according to claim 1, wherein
the compound represented by formula (I) is a compound represented by formula (Ia)

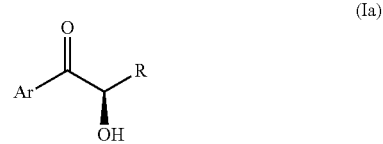

wherein Ar represents a phenyl group optionally substituted by 1 to 3 substituents selected from the group consisting of a halogen atom and a trifluoromethyl group, and R represents a hydrogen atom or an alkyl group having 1 to 12 carbon atoms, and
the compound represented by formula (II) is a compound represented by formula (IIa)

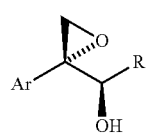

wherein Ar and R are as defined above.

3. The process according to claim 1, further comprising:

a step C of reacting the compound represented by formula (II) with 1,2,4-triazole in the presence of a base to obtain a compound represented by formula (III) or a salt thereof

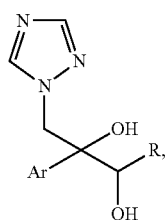

wherein Ar and R are as defined in claim 1.

4. The process according to claim 3, wherein the compound represented by formula (I) is a compound represented by formula (Ia)

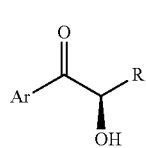

wherein Ar represents a phenyl group optionally substituted by 1 to 3 substituents selected from the group consisting of a halogen atom and a trifluoromethyl group, and R represents a hydrogen atom or an alkyl group having 1 to 12 carbon atoms, the compound represented by formula (II) is a compound represented by formula (IIa)

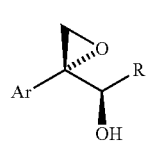

wherein Ar and R are as defined above, and the compound represented by formula (III) is a compound represented by formula (IIIa)

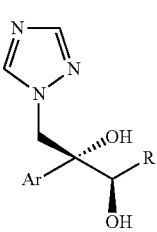

wherein Ar and R are as defined above.

5. The process according to claim 3, further comprising:

a step D of converting a primary or secondary hydroxyl group of the compound represented by formula (III) or a salt thereof into a leaving group to obtain a compound represented by formula (IV) or a salt thereof

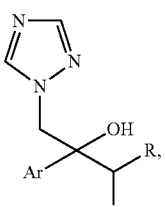

wherein X is a leaving group, and Ar and R are as defined in claim 3.

6. The process according to claim 5, wherein the compound represented by formula (I) is a compound represented by formula (Ia)

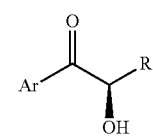

wherein Ar represents a phenyl group optionally substituted by 1 to 3 substituents selected from the group consisting of a halogen atom and a trifluoromethyl group, and R represents a hydrogen atom or an alkyl group having 1 to 12 carbon atoms, the compound represented by formula (II) is a compound represented by formula (IIa)

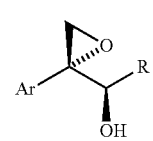

wherein Ar and R are as defined above, the compound represented by formula (III) is a compound represented by formula (IIIa)

(IIIa)

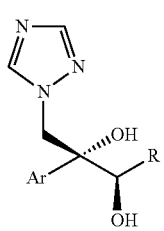

wherein Ar and R are as defined above, and
the compound represented by formula (IV) is a compound represented by formula (IVa)

(IVa)

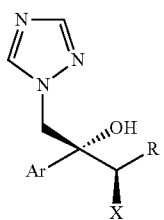

wherein X represents a leaving group, and Ar and R are as defined above.

7. The process according to claim 5, further comprising:

a step E of reacting the compound represented by formula (IV) or a salt thereof with a base to obtain a compound represented by formula (V) or a salt thereof (V)

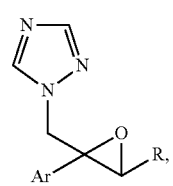

wherein Ar and R are as defined in claim 5.

8. The process according to claim 7, wherein the compound represented by formula (I) is a compound represented by formula (Ia)

(Ia)

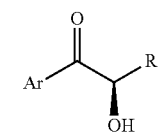

wherein Ar represents a phenyl group optionally substituted by 1 to 3 substituents selected from the group consisting of a halogen atom and a trifluoromethyl group, and R represents a hydrogen atom or an alkyl group having 1 to 12 carbon atoms,
the compound represented by formula (II) is a compound represented by formula (IIa)

(IIa)

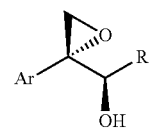

wherein Ar and R are as defined above,
the compound represented by formula (III) is a compound represented by formula (IIIa)

(IIIa)

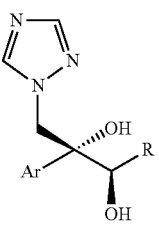

wherein Ar and R are as defined above,
the compound represented by formula (IV) is a compound represented by formula (IVa)

(IVa)

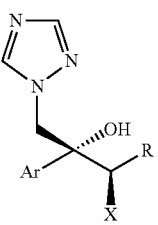

wherein X represents a leaving group, and Ar and R are as defined above, and
the compound represented by formula (V) is a compound represented by formula (Va)

(Va)

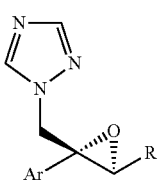

wherein Ar and R are as defined above.

9. The process according to claim 1, further comprising:
a step F of converting a hydroxyl group of the compound represented by formula (II) into a leaving group to obtain a compound represented by formula (VI)

(VI)

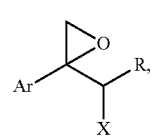

wherein X represents a leaving group, and Ar and R are as defined in claim 1.

10. The process according to claim 9, wherein the compound represented by formula (I) is a compound represented by formula (Ia)

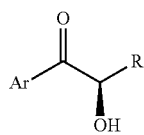

(Ia)

wherein Ar represents a phenyl group optionally substituted by 1 to 3 substituents selected from the group consisting of a halogen atom and a trifluoromethyl group, and R represents a hydrogen atom or an alkyl group having 1 to 12 carbon atoms, the compound represented by formula (II) is a compound represented by formula (IIa)

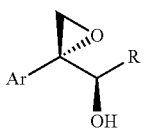

(IIa)

wherein Ar and R are as defined above, and the compound represented by formula (VI) is a compound represented by formula (VIa)

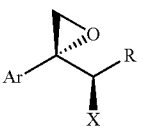

(VIa)

wherein X represents a leaving group, and Ar and R are as defined above.

11. The process according to claim 9, further comprising:

a step G of reacting the compound represented by formula (VI) with 1,2,4-triazole in the presence of a base to obtain a compound represented by formula (V) or a salt thereof

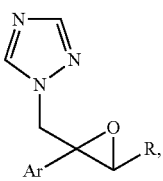

(V)

wherein Ar and R are as defined in claim 9.

12. The process according to claim 11, wherein the compound represented by formula (I) is a compound represented by formula (Ia)

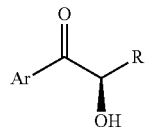

(Ia)

wherein Ar represents a phenyl group optionally substituted by 1 to 3 substituents selected from the group consisting of a halogen atom and a trifluoromethyl group, and R represents a hydrogen atom or an alkyl group having 1 to 12 carbon atoms, the compound represented by formula (II) is a compound represented by formula (IIa)

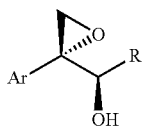

(IIa)

wherein Ar and R are as defined above, the compound represented by formula (VI) is a compound represented by formula (VIa)

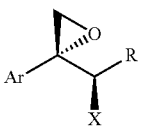

(VIa)

wherein X represents a leaving group, and Ar and R are as defined above, and the compound represented by formula (V) is a compound represented by formula (Va)

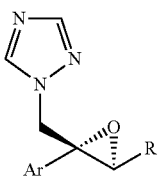

(Va)

wherein Ar and R are as defined above.

13. The process according to claim 1, wherein Ar is a 2,4-difluorophenyl group or a 2,5-difluorophenyl group.

14. The process according to claim 13, wherein R is a methyl group.

15. The process according to claim 14, wherein a solvent for reacting the trimethyl oxosulfonium salt or trimethyl sulfonium salt with the base in the step A is tetrahydrofuran, dimethylsulfoxide, toluene, or a mixed solvent thereof.

* * * * *